(12) United States Patent
Polland

(10) Patent No.: US 7,296,895 B2
(45) Date of Patent: Nov. 20, 2007

(54) SEQUENTIAL SCANNING WAVEFRONT MEASUREMENT AND RETINAL TOPOGRAPHY

(75) Inventor: Hans Joachim Polland, Wolfratshausen (DE)

(73) Assignee: Bausch & Lomb Incorporated, Rochester, NY (US)

(*) Notice: Subject to any disclaimer, the term of this patent is extended or adjusted under 35 U.S.C. 154(b) by 445 days.

(21) Appl. No.: 10/498,455

(22) PCT Filed: Dec. 13, 2002

(86) PCT No.: PCT/EP02/14258

§ 371 (c)(1),
(2), (4) Date: Nov. 15, 2004

(87) PCT Pub. No.: WO03/051187

PCT Pub. Date: Jun. 26, 2003

(65) Prior Publication Data

US 2005/0163455 A1    Jul. 28, 2005

Related U.S. Application Data

(60) Provisional application No. 60/340,529, filed on Dec. 14, 2001.

(51) Int. Cl.
*A61B 3/10* (2006.01)

(52) U.S. Cl. ............ 351/212; 351/211; 351/239; 351/243; 351/247

(58) Field of Classification Search ........... 351/211, 351/212, 239, 243, 247
See application file for complete search history.

(56) References Cited

U.S. PATENT DOCUMENTS 6,634,750 B2 *  10/2003  Neal et al. ............. 351/211

* cited by examiner

*Primary Examiner*—Evelyn A. Lester

(57) ABSTRACT

An improved sequential scanning method and apparatus for measuring wavefront aberration involves angularly displacing a measurement beam from a parallel beam striking the corneal surface at a desired location and using the displacement of an image on a detector between the angularly displaced beam and a reference beam to obtain a more accurate wavefront measurement than provided by the displacement between the parallel beam and a reference beam conventionally used for such wavefront aberration measurement. A method and related apparatus for determining a retinal topography relies on using the improved measurement method and apparatus in conjunction with other ocular data to determine changes in the bulbous length of the eye based upon retinal image displacement.

12 Claims, 4 Drawing Sheets

SEQUENTIAL SCANNING WAVEFRONT MEASUREMENT AND RETINAL TOPOGRAPHY

This application claims priority to U.S. Provisional Application Ser. No. 60/340,529 filed on Dec. 14, 2001, which is hereby incorporated by reference in its entirety.

BACKGROUND OF THE INVENTION

1. Field of the Invention

The invention relates generally to ophthalmic wavefront and topography measurement and more particularly to devices and methods for improved wavefront measurement using a sequential scanning technique, and to an apparatus and method for making real topography measurements.

2. Description of Related Art

Various ophthalmic diagnostic devices and techniques are known and available for mapping the physical and optical characteristics of the eye. Physical data such as corneal topology, pachymetry, refraction and other parametric data can be obtained from corneal topography systems such as the Orbscan II corneal topography system (Bausch & Lomb Incorporated, Rochester, N.Y.). Optical information such as the wavefront aberration of the eye can also be obtained from various devices and measurement methodologies. One such aberrometer uses a Hartmann-Shack wavefront sensor to measure ocular wavefront aberrations over the entire optical zone of the eye in a single pass. This is accomplished by illuminating a point on the retina with a very small diameter laser beam and focussing the outgoing light from the exit pupil of the eye with an array of lenslets onto a detector. Aberrations from the wavefront cause the focal spots on the detector that are created by the lenslet array to be displaced from the positions of an unaberrated wavefront passing through the lenslet array. These displacements allow the direct calculation of the wavefront error. Several well-known disadvantages of the Hartmann-Shack type device include dynamic range/resolution tradeoffs, low signal to noise ratios, suspect readings in pathologic eyes, and others known to those skilled in the art.

One of several alternative techniques for measuring wavefront aberrations derives from a psychophysical ray tracing approach originally attributed to Scheiner and based upon the Scheiner's disc concept. In summary, this concept is based on the adjustment of the direction of light from an image coming into the eye until the retinal image is aligned with the retinal image produced by a reference input light direction. A further explanation and more detailed description can be found in MacRae et aL, *Customized Corneal Ablation, The Quest for Super Vision*, Chapter 16, Slack Incorporated (2001). The Scheiner concept was further developed by Penney et al., and their device came to be known as the spatially resolved refractometer (SRR). The SRR operates by having a patient view a point object introduced to the eye at 37 selected positions on the cornea in a sequential fashion and asking the patient when tie image is focussed at a particular reference location as the directionality of the input object is changed. The resulting ray deviations provide wavefront slope information from which the wavefront can be determined.

A variant of the SRR concept adapted by Tracey Technologies LLC (Bellaire, Tex.) is referred to as sequential scanning or thin beam ray tracing. The sequential scanning technique relies on sequentially inputting a small diameter, collimated laser beam into the eye at selected points on the corneal surface and ultimately measuring the displacement $(\Delta x, \Delta y)$ of each image spot on the retinal surface from a reference retinal spot location $(x_0, y_0)$. The displacement errors are a direct measure of the transverse aberration for each particular point in the entrance pupil. With appropriate optics and relatively simple algebraic computing means, the displacements can be measured on a detector and the wavefront aberration calculated.

While the sequential scanning method for wavefront aberration measurement has certain advantages over alternate wavefront measuring techniques, this method suffers from some inherent shortcomings that principally relate to relying upon certain assumptions about the eye. These assumptions particularly relate to determining a correct length of the ocular bulbous; and, second, the assumption that the retinal surface is a flat plane at the posterior surface of the eye. In reality, however, the retinal surface is at best a curved envelope having a topography of irregular hills and valleys The inventors believe this to be especially evident in diseased retinas and at the foveal blind spot. Owing to the non-flat profile of the retina, the measurement of wavefront aberrations made using input beams that are parallel to a reference measurement axis such as the visual axis or the optical axis of the eye will lose accuracy as the retinal location of an image deviates from the retinal plane to follow the real retinal envelope profile.

Accordingly, the inventors have recognized a need for a way to improve the accuracy of the sequential scanning wavefront technique; and for a better understanding of the retinal topography around a retinal reference location and the ability to measure this topography.

SUMMARY OF THE INVENTION

An embodiment of the invention is directed to an improved method for measuring wavefront aberration based upon a known sequential scanning technique for measuring such aberration. The known technique relies on inputting a reference beam to the eye that is parallel to a known reference axis and which intersects the eye at a known corneal location. The light is imaged onto the retina and is scattered therefrom out through the eye and is imaged by a lens onto a detector where the position of the image is recorded. A second beam is input to the eye parallel to the reference axis and displaced a known distance from the reference beam such that it strikes the eye at a desired corneal location. The second beam is imaged on the retina at a different retinal location than the first beam, is scattered, and is likewise imaged onto a detector. The displacement between the second image and the first image on the detector is then used in a known manner to calculate the wavefront aberration of the eye. The improvement, according to the invention, relies on inputting a third beam to the eye at the same position as the second beam on the corneal surface but inclined at an angle with respect to the reference axis such that the retinal image location of the third image is made to coincide with the retinal image location of the first image. The third image light scattered from the retina is imaged onto the detector and the displacement between the third image location and the reference image location is used in a known manner to provide a more accurate measurement of the wavefront than that provided by the second image.

In another embodiment, a method and device are described for determining a topographical variation of the retinal surface. Based upon the known focussing power of the eye and parametric information such as bulbous length, a wavefront aberration measurement indicative of a change in spherical focussing power can be used in a known manner to determine the variation in the bulbous length that would give rise to the measured changed in spherical focussing power. Referring again to the embodiment described above, measurements at the detector can be used to determine the lateral displacement on the retinal surface corresponding to the displacement of image spots from the reference beam and the second beam. The more accurate measurement obtained from the third beam, as described above, can then be used to determine the change in the bulbous length giving rise to the refined measurement error. The difference in the bulbous length based on this measured error will be indicative of the retinal topography at that particular image location on the retina. Thus, the topography of the retina can be mapped corresponding to the various locations on the corneal surface where the input beams are introduced to the eye.

The embodiments described above have a basis in conventional sequential scanning techniques and apparatus and comprise improvements and modifications to known systems and methods for improving the accuracy of conventional measurements and providing additional parametric measurements of the eye.

These and other objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

DETAILED DESCRIPTION OF A PREFERRED EMBODIMENT OF THE INVENTION

Figure 1A:
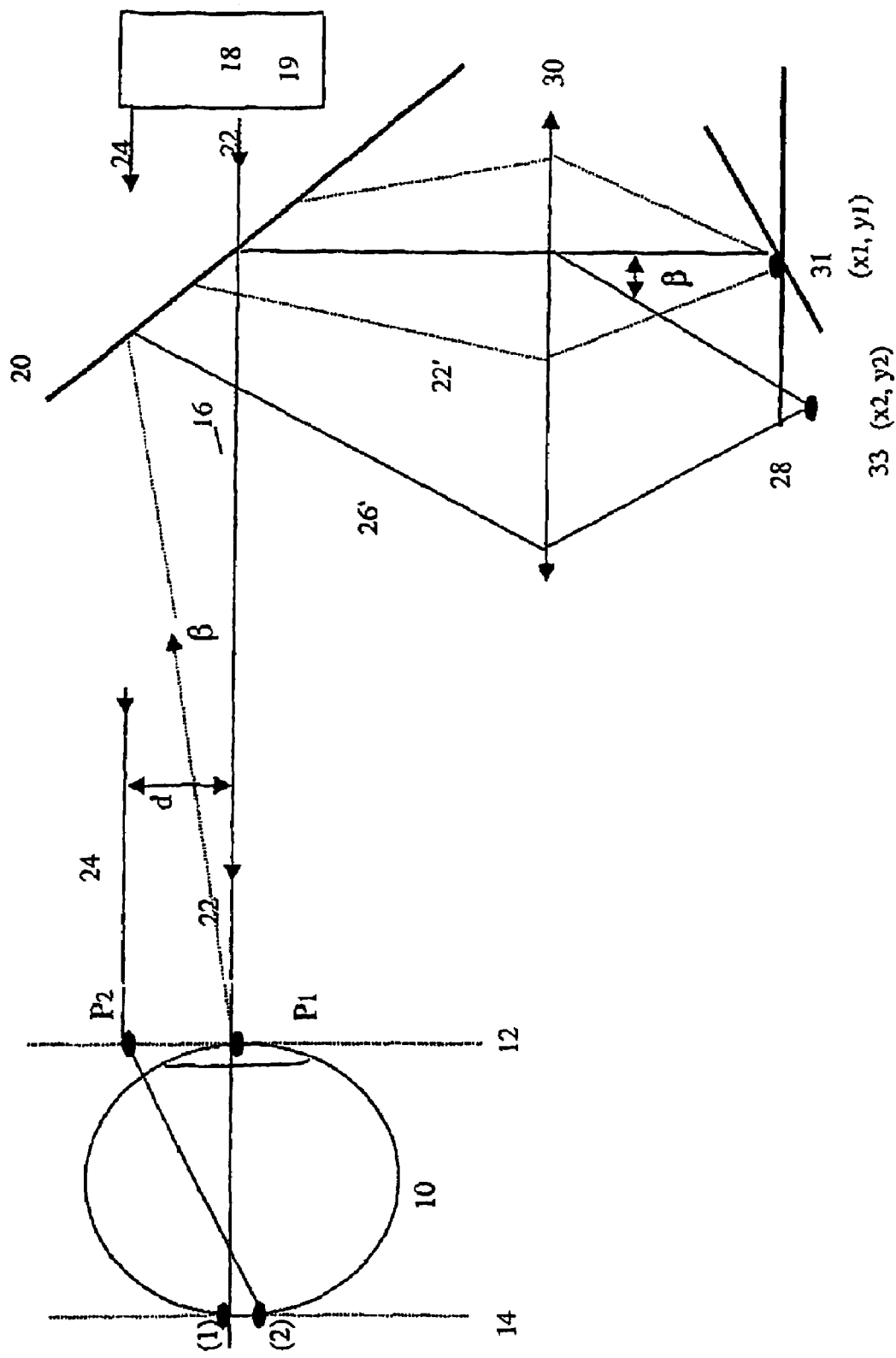
FIGS. 1a and 1b are schematic illustrations showing light ray paths illustrating a system and method according to embodiments of the invention.
Figure 1B:
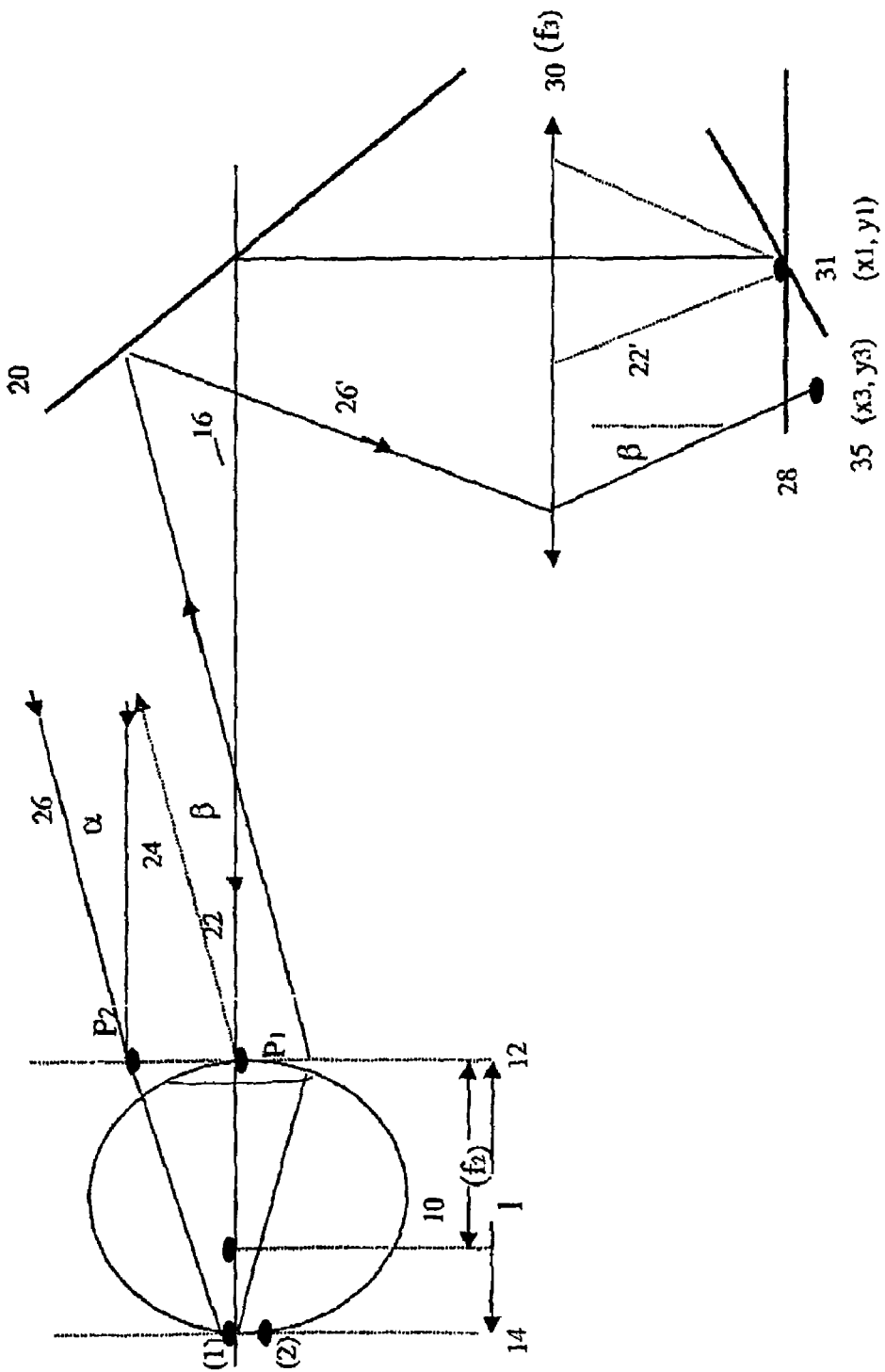

A preferred embodiment of the invention for more accurately measuring a wavefront aberration of an eye using a sequential scanning technique is described in connection with FIGS. 1a and 1b. In FIG. 1a, an eye 10 to be measured has a representative anterior corneal plane 12 and a representative retinal plane 14. A reference axis 16 is represented by the visual axis of the eye as it is fixated on a target 18. A beam splitter 20 allows first and second parallel input beams 22, 24 to reach the cornea from a laser source 19 incorporating a scanning apparatus (not shown), and directs return beams scattered from the retinal plane through an imaging lens 30 to a detector 28. First and second beams 22, 24 are preferably collimated laser beams having a diameter between about 0.2 mm to 2.0 mm and more preferably between about 0.4 mm to 0.5 mm. The wavelength range of the input beam is preferably between about 400 nm to 1200 nm and more preferably in the near IR range of about 700 nm to 900 nm.

A person having skill in the an will appreciate that the setup comprises all of the device hardware and software for measuring wavefront aberrations of the eye with a sequential scanning-type wavefront analyzer. The device components generally include means for sequentially inputting a reference light beam into the eye at a selected location on the cornea having a propagation path coincidence with a reference axis, and a plurality of measurement light beams into the eye at selected locations on the cornea having propagation paths that are mutually parallel and parallel to the reference axis. In addition, the device generally comprises means for capturing light from each of the input beams scattered from different locations of the retinal surface and imaging his light at a desired external location, a detector for receiving the imaged light and detecting a displacement of the image from a reference image on the detector, and hardware/software for calculating the wavefront aberration corresponding to a particular corneal location from the image displacement data at the detector plane. The actual layout of a device comprises engineering designs flat are not crucial to an understanding of the instant invention and, therefore, are not discussed in further detail.

Referring again to FIG. 1a, a known method for measuring the wavefront aberration of the eye by a sequential scanning technique is as follows: A first input laser beam 22 is input to the eye 10 along the patient's visual axis 16 and approximately through the center of the pupil. The first input beam 22 intercepts the corneal surface at location $P_1$. The eye's optical system focuses this beam at location (1) on retinal plane 14 for an emmetropic eye. If myopic or hyperopic defocus is not corrected, the actual focal position of the incoming light would be located at $f_2$ as shown in FIG. 1b rather than at location (1) on retinal plane 14. Light at position (1) on the retinal plane 14 is scattered and exits the eye along its input path whereupon it is directed by optic 20 through imaging lens 30. The imaging lens images the scattered light onto the detector 28 at reference location 31 having reference position coordinates $(x_1, y_1)$.

A second sequentially input beam 24 parallel to the beam path of 22 and displaced therefrom by a distance d strikes the cornea at a location $P_2$. Assuming, for clarity of description, that eye 10 is myopic, the second measurement beam 24 crosses the reference axis 16 at $f_2$ (FIG. 1b) and strikes the retinal plane 14 at position (2). Location (2) on retinal plane 14 is displaced from location (1) by a distance B. The second beam 24 is scattered by the retina and exits the eye in a general direction indicated by the angle β whereupon it is imaged as a spot 33 onto the detector surface 28 at a position $(x_2, y_2)$. The displacement of the imaged spot 33 from reference spot 31, represented by $(x_{2-1}, y_{2-1})$, is calculated in known manner to provide wavefront aberration information corresponding to the points $P_1$ and $P_2$ on the corneal surface. In an actual system, a plurality of measurement beams $24_n$ would be sequentially input to the eye at different locations $P_n$ on the cornea so that the wavefront aberration could be mapped over the entire desired surface area of the cornea.

Due to the fact that the retinal plane 14 is not actually a planar surface but rather can be thought of as an envelope having topographical variation over its surface, the wavefront aberration measurement derived from the displacement of the image spots on the detector does not necessarily provide as much measurement accuracy as may be desired, e.g., a deviation of the retina surface by 100 μm from the planar surface results in a change in the sphere of approximately 0.3 dpt. According to an embodiment of the invention, the wavefront measurement accuracy can be improved upon as follows. The following definitions, with reference to the Figures, will assist the reader in understanding the invention.

d=displacement of second measurement beam from first reference beam on the corneal surface;

$f_2$=focal length of emmetropic eye (approximately 55D);

l=length of eye along the reference axis from the corneal plane 12 to the retinal plane 14 (typically about 25 mm ±4 mm), B-distance along retinal plane between reference image (1) and displaced reference image (2);

$f_3$=focal length of imaging lens 30;

x-hd 11, $y_{11}$ displacement of imaged beam spot from reference position $x_1$, $y_1$ on detector;

β=general direction angle of scattered light exiting the eye from parallel input measurement beam at the center of the cornea; and α=angle of an additional measurement beam used for improving the accuracy of the wavefront measurement according to an embodiment of the invention.

Referring again to FIG. 1b, an adjustable additional measurement beam 26 is input to the eye at an intercept point on the corneal plane that is the same as the intercept point $P_2$ of second input beam 24. The angle α of the adjustable beam with respect to a reference axis is adjusted such that an object in light beam 26 is imaged on the retinal plane as close as possible to location (1) (i.e., where the reference beam 22 strikes the retinal plane). The scattered return beam 26' is imaged by imaging lens 30 on the detector as image spot 35 with coordinates $x_3$, $y_3$. By generating a wavefront measurement from the displacement data $\Delta x_{3-1}$, $\Delta y_{3-1}$, a more accurate determination of the wavefront corresponding to the $P_2$ corneal position can be made. This procedure is then repeated for each displaced input beam to map the corneal surface aberration correspondence as desired. Although the above discussion was made with reference to two-dimensional coordinates, it will be appreciated that vector calculations will be necessary to map an actual condition.

As an example illustrating the above description, assume that the original sequential scanning method results in a 10% wavefront measurement error and thus a 10% error in the angular deviation of the scattered beam and similarly with the displacement, B, on the retinal plane. Further, assume for illustration that the real error of the eye to be measured has a value of −10D, while the input light is parallel (0D). The measured aberration will thus be −9D. According to the invention, the adjustment beam is input to the eye at an angle corresponding to a −9D aberration. The spot displacement on the detector, $\Delta x_{3-1}$, will be approximately equal to $0.1\Delta x_{2-1}$, and Δβ will approximately be 0.1β. Since the wavefront aberration of −9D was directly measured from β, the Δβ contribution is approximately −0.9D giving a measured aberration value of spherical defocus as −9.9D Since it takes approximately 50 ms to make a single sequential scanning measurement the total time for the additional measurement is approximately 100 ms. Optionally, the additional measurement process could be performed iteratively, for example, a fourth adjustment beam, α', could be input at an angular divergence corresponding to −9.9D just measured. The resulting $\Delta x_4$ would approximately equal $0.1\Delta x_3$ which would approximately equal $0.01\Delta x_2$. This would give rise to a Δβ, of −0.09D resulting in a measured spherical defocus of −9.99D for the assumed real value of defocus error equal to −10D. Such a three times iterative procedure would take approximately 150 ms to complete.

Based upon the definitions given above, and with reference to the figures, simple algebraic geometry yields the following relationships:

$$\beta = \Delta x_{2-1}/f_3;$$

$$\beta = n_c[1-f_2d]/f_21;$$

$$B = 1\Delta x_{2-1}/f_3$$

. . . from paraxial optics:

$$1/s = n_c/f_2 - n_c/1 = n_c[1-f_2]/f_21; \text{ (image length of object on retina outside the eye)}$$

$$\alpha \approx d/s = n_c[1-f_2d]/f_21 = \beta;$$

$$|\alpha| \approx |\beta|.$$

Figure 2:
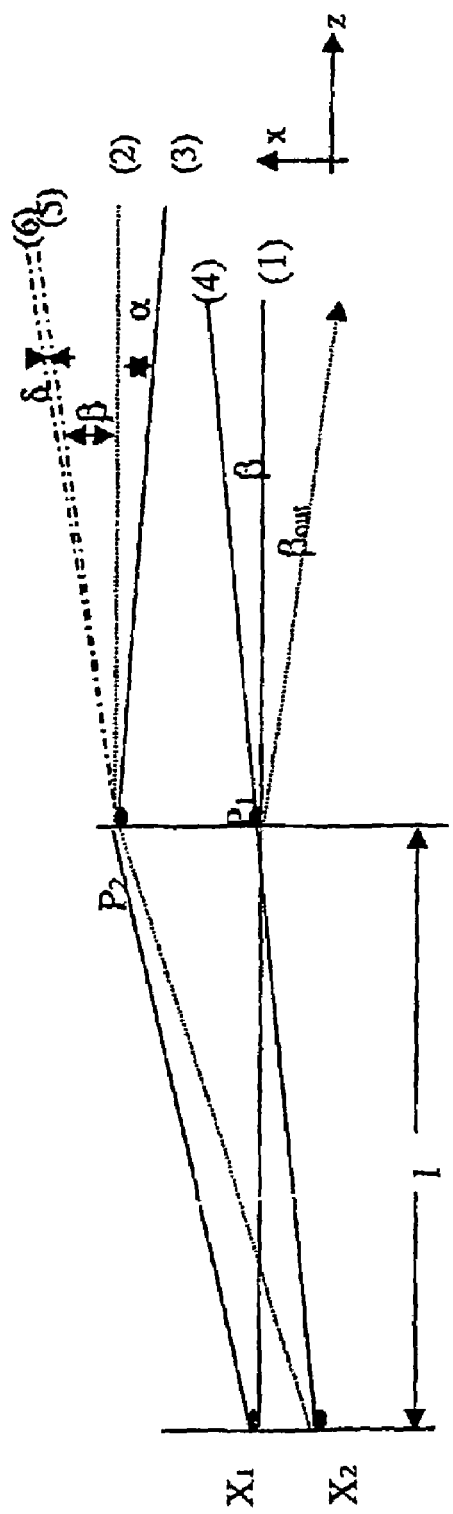
FIG. 2 is a ray trace drawing showing different light paths according to an embodiment of the invention.
Figure 3:
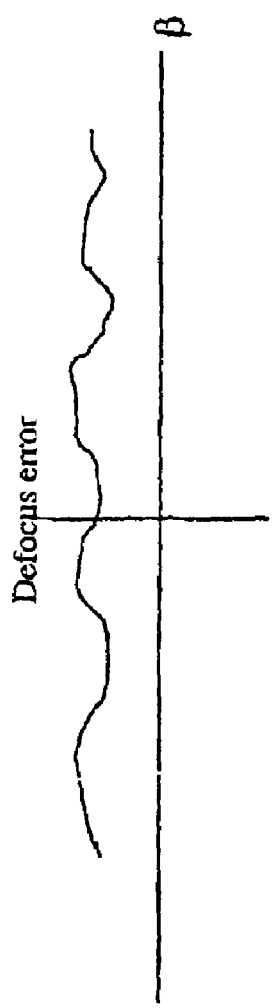
FIG. 3 shows a plot of the relationship between spherical defocus error and the direction of light rays exiting the eye.

Another embodiment of the invention is directed to measuring a topographical variation of the retina at points along the retinal surface. This follows directly from the description set forth above and is explained in detail with reference to FIG. 2. It is known from the description above that when a first beam (1) parallel to the visual axis strikes the cornea at point $P_1$ and is scattered off the retinal surface at $X_1$, and a second parallel beam (2) displaced from the first beam strikes the cornea at point $P_2$ and scatters off of the retina at point $X_2$ and exiting the eye at angle $\beta_{out}$, that the displacement of the image spots on a detector plane between beams (1) and (2) give rise to the spherical defocus error corresponding to point $P_2$ on the cornea. According to the embodiment of the invention described above, when a third beam (3) is introduced at point $P_2$ on the cornea and scattered from point $X_1$ on the retinal surface, the angle α and the displacement on the detector between beams (1) and (3) gives rise to a refined spherical refraction error corresponding to point $P_2$ on the cornea. According to the instant embodiment, a fourth beam (4) is input to the eye at corneal position $P_1$ and angle β where it scatters from the retinal surface at $X_2$. A fifth beam (5) parallel to the fourth beam (4) is then input to the eye at corneal position $P_2$. Then a sixth beam (6) displaced from the fifth beam (5) by a small angle δ is introduced at point $P_2$ to provide an even more refined spherical refraction error from position $X_2$ on the retina and corresponding to location $P_2$ on the cornea FIG. 3 shows in generalized form the variation in spherical defocus measurement as a function of the angle β provided by the instant embodiment. If in fact the corneal surface were a flat planar surface, FIG. 3 would show a straight horizontal line indicative of no variation in spherical refractive error as a function of retinal location. If the spherical power of the eye is taken to be approximately 55D, and the eye length, 1, approximately equal to 25 mm, then a variation in spherical defocus of 1D measured according to the technique described above will correspond to a displacement between $X_1$ and $X_2$ in the z-direction of 1/55 D×25 mm/$n_c$≈330 μm. With a measurement accuracy of 0.05D, this provides a resolution in the z-direction of approximately 17 μm. Since a ΔX value on the retinal surface can be expressed as $(\alpha 1)/n_c$ where α is the known input angle, each Time a refractive error is measured at the detector for a known ΔX value on the retina, a z-value at that point on the retinal surface can be approximated from the correspondence of a one diopter error approximately equal to 330 μm displacement in the z-direction. Thus, the topography of the cornea can be mapped This resolution is on the order of that provided by OCT measurements.

Figure 4:
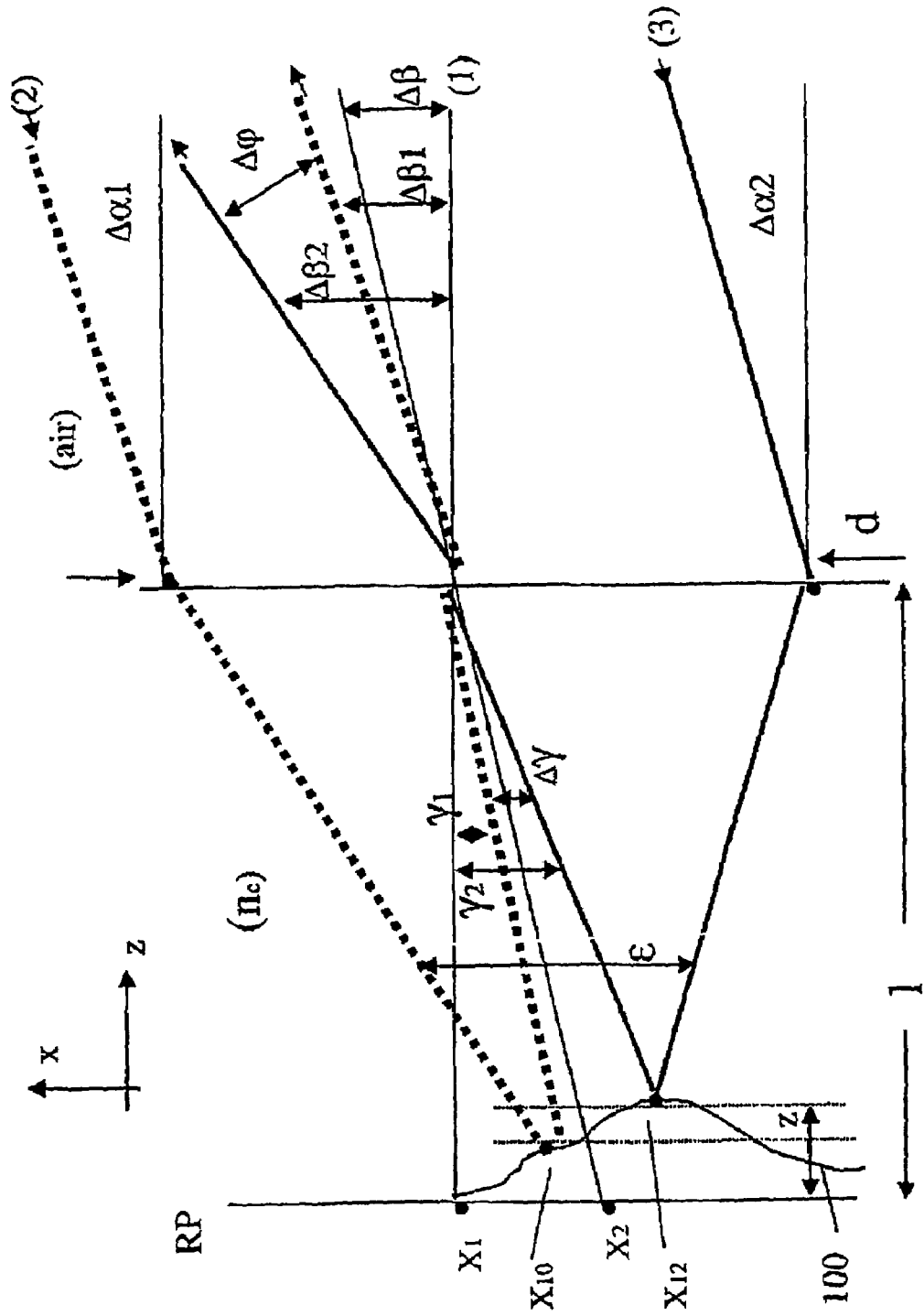
FIG. 4 is a schematic illustration showing light path rays in an embodiment of the invention directed to retinal topography measurement.

A more detailed description of a retinal topography embodiment according to the invention is now provided with reference to FIG. 4. If the retina were a retinal plane RP, then the original beams (1) and (2) would scatter from the retinal surface at positions $X_1$ and $X_2$ respectively. The difference $\Delta X_{2-1}$ could be expressed as $(\Delta \alpha/n) \times 1$. However, due to the eye's aberrations and a non-planar retinal surface 100, input beams (2) and (3) are scattered off of retinal positions $X_{10}$ and $X_{12}$, respectively. If the retina were flat, the input beam (3) at angle $\Delta \alpha_2$ based upon the wavefront error measured from $\Delta \alpha_i$ would provide the same signal on the detector for $\Delta \alpha_2$ as for $\Delta \alpha_1$. In this case, $\Delta \beta_1$ and $\Delta \beta_2$ would be equal. However, the angular dependencies, as shown, are as follows, and $\Delta \psi$ can be measured at the detector.

$$\Delta \psi = (\Delta \beta_2 - \beta_1);$$

$$\epsilon = d/1 = \Delta X_{10-12}/z;$$

$$\Delta X_{10-12} = dz/1;$$

$$\Delta \gamma = \Delta X_{10-12}/(1-z) \equiv \Delta X_{10-12} 1 = dz/1^2;$$

$$\Delta \psi = n_c \Delta \gamma = dz/1^2; \text{ and}$$

$$z = 1^2 \Delta \psi / n_c d.$$

For example, assuming d=5 mm, $n_c$=1.336, 1=25 mm and z=20 μm, $\Delta \psi = 2.14 \times 10^{-4}$ rad=0.012°.

Based on the foregoing description, it can be seen that the procedure according to the invention allows the retinal topography and wavefront aberration to be measured in a single system. Accordingly, an embodiment of the invention is directed to a system for measuring the retinal topography and wavefront aberration of an optical system, preferably a person's eye. It will be further appreciated that the system is similar to the system described above for an improved sequential scanning wavefront sensor with the addition that additional measurement beams can be input to the eye at various selected input angles allowing various degrees of measurement resolution to be obtained from the displacement of image spots on the detector.

While various advantageous embodiments have been chosen to illustrate the invention, it will be understood by those skilled in the art that changes and modifications can be made therein without departing from the scope of the invention as defined in the appended claims.

I claim:

1. In a method for measuring a wavefront aberration of an eye in which a first, reference, object beam projected parallel to a known reference axis is input to the eye at a first, reference location ($P_1$) on a cornea of the eye such that the first beam is scattered from a location (1) on the retinal surface and further imaged onto a detector at a reference position ($x_1$, $y_1$), and at least a sequential, second object beam parallel to and displaced a known amount (d) from the reference beam is projected into the eye at a second location ($P_2$) on the cornea, is scattered from a location (2) on the retinal surface and further imaged onto the detector at a second position ($x_2$, $y_2$), such that a displacement ($\Delta x_{2-1}$, $\Delta y_{2-1}$) can be measured and from which wavefront aberration information can be calculated, the improvement characterized by:

inputting a third beam corresponding to each sequential second beam at an angle ($\alpha$) to the reference axis that enters the cornea at the same location as each second beam ($P_2$) and is scattered from a location (3) on the retinal surface substantially corresponding to location (1) and further imaged onto the detector at a third position ($x_3$, $y_3$), such that a displacement ($\Delta x_{3-1}$, $\Delta y_{3-1}$) can be measured and the wavefront aberration calculated corresponding to location $P_2$ on the cornea, whereby the wavefront aberration for cornea location $P_2$ from the third beam data is more accurate than the corresponding measurement from the second beam measurement.

2. The method of claim 1, wherein the input beams each have a diameter between about 0.2 to 2 mm.

3. The method of claim 1, wherein the input beams each have a diameter between about 0.4 to 0.5 mm.

4. The method of claim 1, wherein the input beams have a wavelength between about 400 to 1200 nm.

5. The method of claim 1, wherein the input beams have a wavelength between about 700 to 900 nm.

6. The method of claim 1, wherein the reference axis is a fixating visual axis of the eye.

7. The method of claim 1, wherein the reference axis is an optical axis of the eye.

8. The method of claim 1, further comprising inputting a sufficient number of second and third input beams at different corneal locations ($P_n$) to wavefront map a desired surface area of the cornea.

9. In an improved sequential scanning device for making a wavefront measurement of an eye, wherein the device includes means for sequentially inputting a reference light beam into the eye at a selected location on a cornea of the eye having a propagation path coincident with a reference axis, and a plurality of measurement light beams into the eye at selected locations on the cornea having propagation paths that are mutually parallel and parallel to the reference axis; means for capturing light from each of the input beams scattered from different locations of a retinal surface of the eye and imaging said light at a desired external location; a detector for receiving said imaged light and detecting a displacement of the image from a reference image; and calculation means for calculating wavefront aberration information from the image displacement that corresponds to the input location on the cornea, the improvement comprising:

means for sequential inputting a plurality of additional measurement beams, each of which corresponds to a measurement beam, into the eye at locations on the cornea that correspond to the measurement beams and which strike the retinal surface at a location substantially where the reference beam strikes the retinal surface, such that each of the additional measurement beams are imaged on the detector at a displacement from the reference image, and wherein the calculation means calculates the wavefront aberration information from the additional image displacement corresponding to the input locations on the cornea.

10. A method for determining a topographic variation of a retinal surface of an eye comprising:

inputting a first object beam projected parallel to a known reference axis to the eye at a first location ($P_1$) on a cornea of the eye such that the first beam is scattered from a location (1) on the retinal surface and further imaged onto a detector at a reference position ($x_1$, $y_1$);

inputting a second object beam parallel to and displaced a known amount (d) from the reference beam to the eye at a second location ($P_2$) on the cornea, wherein it is scattered from a location (2) on the retinal surface and further imaged onto a detector at a second position ($x_2$, $y_2$);

making a first spherical refractive error measurement corresponding to ($\Delta x_{2-1}$, $\Delta y_{2-1}$);

inputting a third beam to the eye at a selected angle ($\alpha$) to the reference axis at the same location as the second beam ($P_2$) which is scattered from a location (3) on the retinal surface substantially corresponding to location (1) and further imaged onto the detector at a third position ($x_3$, $y_3$);

making a second spherical refractive error measurement corresponding to ($\Delta x_{3-1}$, $\Delta y_{3-1}$); and determining, for a $\Delta X_{2-1}$ displacement on the retinal surface, a $\Delta l$ change in the length of the eye.

11. The method of claim 10, comprising sequentially inputting a plurality of second and third beams corresponding to a plurality of locations on the corneal surface.

12. A device that provides retinal topography information, comprising:

means for sequentially inputting a reference light beam into an eye at a selected location on a cornea of the eye having a propagation path coincident with a reference axis, and a plurality of measurement light beams into the eye at selected locations on the cornea having propagation paths that are mutually parallel and parallel to the reference axis;

means for capturing light from each of the input beams scattered from different locations of the retinal surface of the eye and imaging said light at a desired external location;

a detector for receiving said imaged light and detecting a displacement of the image from a reference image;

calculation means for calculating wavefront aberration information from the image displacement that corresponds to the input location on the cornea;

means for sequential inputting a plurality of additional measurement beams, each of which corresponds to a measurement beam, into the eye at locations on the cornea that correspond to the measurement beams and which strike the retinal surface at a location substantially where the reference beam strikes the retinal surface, such that each of the additional measurement beams are imaged on the detector at a displacement from the reference image, and wherein the calculation means calculates the wavefront aberration information from the additional image displacement corresponding to the input locations on the cornea, further wherein the calculation means uses the wavefront aberration information from the additional image displacement and ocular parametric information for mapping the retinal topography.

* * * * *